United States Patent [19]

Goettsche

[11] Patent Number: 5,021,459

[45] Date of Patent: Jun. 4, 1991

[54] WOOD PRESERVATIVES

[75] Inventor: Reimer Goettsche, Baden-Baden, Fed. Rep. of Germany

[73] Assignee: Dr. Wolman GmbH, Sinzheim, Fed. Rep. of Germany

[21] Appl. No.: 432,178

[22] Filed: Nov. 1, 1989

[30] Foreign Application Priority Data

Nov. 24, 1988 [DE] Fed. Rep. of Germany ....... 3839640

[51] Int. Cl.$^5$ ........................................... A01N 33/02
[52] U.S. Cl. ................................................... 514/663
[58] Field of Search ................... 514/231.2, 232.8, 937, 514/663; 406/18.32

[56] References Cited

U.S. PATENT DOCUMENTS

| | | | |
|---|---|---|---|
| 2,204,511 | 11/1938 | Ralston et al. | 514/554 |
| 3,565,927 | 2/1971 | Wakeman et al. | 260/404 |
| 3,893,825 | 7/1975 | Goeller | 44/408 |
| 3,928,606 | 12/1975 | Pommer et al. | 514/231.2 |
| 3,973,018 | 8/1976 | Pommer et al. | 514/231.2 |
| 4,155,872 | 5/1979 | Shigehiro et al. | 252/299.2 |
| 4,764,214 | 8/1988 | Marx et al. | 106/18.32 |
| 4,908,362 | 3/1990 | Goettsche et al. | 514/231.2 |

FOREIGN PATENT DOCUMENTS

| | | |
|---|---|---|
| 066196 | 1/1983 | European Pat. Off. . |
| 129211 | 7/1984 | European Pat. Off. . |
| 0025961 | 8/1984 | European Pat. Off. . |
| 135112 | 2/1985 | European Pat. Off. . |
| 147976 | 7/1985 | European Pat. Off. . |
| 223095 | 5/1986 | European Pat. Off. . |
| 193890 | 8/1986 | European Pat. Off. . |
| 277556 | 8/1988 | European Pat. Off. . |
| 0316602 | 5/1989 | European Pat. Off. . |
| 2633874 | 7/1976 | Fed. Rep. of Germany ... 514/231.2 |
| 656747 | 3/1981 | Fed. Rep. of Germany . |
| 299405 | 1/1982 | Fed. Rep. of Germany . |
| 461513 | 2/1984 | Fed. Rep. of Germany . |
| 229297 | 11/1985 | Fed. Rep. of Germany ... 514/231.2 |
| 3507420 | 9/1986 | Fed. Rep. of Germany . |
| 3613254 | 10/1987 | Fed. Rep. of Germany . |

OTHER PUBLICATIONS

E. H. Pommer, Pesticide Science, vol. 15, pp. 285–295, 6/3/84.

A. Sujan et al., Chemical Abstracts, vol. 95, pp. 8,24, 8/81.

Chemical Abstracts, vol. 81, pp. 2, 15, 7/74, Columbus, Ohio.

Chemical Abstracts, vol. 78, pp. 1,8, 1/73, Columbus, Ohio.

Chemische Brichte, vol. 115, 1982, p. 1.

Chemical Abstracts, vol. 107, pp. 20, 16, 11/87.

L. J. Shu et al., Chemical Abstracts, vol. 96, No. 1, 1/4/82, Columbus, Ohio.

*Primary Examiner*—Stanley J. Friedman
*Assistant Examiner*—Kevin Weddington
*Attorney, Agent, or Firm*—Oblon, Spivak, McClelland, Maier & Neustadt

[57] ABSTRACT

Wood preservatives containing a dimethylalkylamine, tridemorph, fenpropemorph or a mixture thereof, an emulsifier and a water-insoluble acid or a salt thereof, and a method for protectin wood from fungi.

15 Claims, No Drawings

WOOD PRESERVATIVES

The present invention relates to water-soluble wood preservatives for the protection of wood, in particular of fresh wood, for example freshly sawn timber in sawmills or freshly felled roundwood in the forest.

It is known that dimethylalkylamines, 4-(3-p-tert-butylphenyl) -2-methylpropyl)-2,6-cis-dimethyl-morpholine (tridemorph) can be used, for example in the form of their salts, for wood preservation (DE 36 13 254.3 and DE 35 07 420.5).

We have found that wood preservatives which contain (a) a dimethylalkylamine, N-tridecyl-2,6-dimethyl-morpholine, 4-(3-(para-tert-butylphenyl)-2-methylpropyl) -2,6-cis-dimethylmorpholine or a mixture thereof.

(b) a water-insoluble acid and (c) an emulsifier have a very good action against wood pests, in particular against fungi, which is better than the action of the known wood preservatives. The novel wood preservatives are water-soluble. They are used in the form of aqueous impregnating solutions, which are prepared from the wood preservatives (concentrates) by dilution with water. The present invention relates both the to concentrates and to the dilute aqueous solutions (impregnating solutions) obtainable therefrom by dilution with water. The novel wood preservatives are suitable for protecting wood, in particular fresh wood, as obtained, for example, as freshly sawn wood in sawmills or as freshly felled roundwood in the forest.

A dimethylalkylamine is an N,N-dimethyl-N-alkyl-amine where the alkyl radical is of, for example, 6 to 20, preferably 12 to 14, carbon atoms. In addition to the pure dimethylalkylamines, it si also possible to use mixtures, for example mixtures of dimethyl-$C_{12}$-alkylamine and dimethyl-$C_{14}$-alkylamine (dimethylalkyl-$C_{12}/C_{14}$-amine).

The emulsifiers used may be ionic or nonionic emulsifiers. Quaternary ammonium compounds, fatty amine salts (for example coconut fatty amine salts, oleylamine salts or stearylamine salts), ethoxylated alkylamines (for example those based on coconut fatty amine or $C_{10}$-$C_{18}$-alkylamine) and N-alkyl-1,3-diaminopropane are particularly suitable.

A quaternary ammonium compound is, for example, a compound of the general formula $(R^1R^2R^3R^4N)^+Z^-$, where $R^1$ is alkyl of 8 to 20, in particular 12 to 20, carbon atoms or benzyl, which is unsubstituted or substituted by $C_1$-$C_{20}$-alkyl or halogen, $R^2$ is $C_1$-$C_6$-alkyl or $C_3$-$C_9$-alkoxy-alkyl, $R^3$ is $C_1$-$C_6$-alkyl or $C_3$- or $C_4$-alkoxy and $R^4$ is $C_1$-$C_{20}$-alkyl, or two of the radicals $R^1$ to $R^4$, together with the nitrogen atom, form a heterocyclic radical which contains 4 or 5 carbon atoms, 1 or 2 nitrogen atoms and one, two or three double bonds, the carbon atoms being unsubstituted or substituted by $C_1$-$C_4$-alkyl or halogen and Z being an acid radical.

A water insoluble acid is, for example, an aliphatic $C_5$-$C_{20}$-carboxylic acid, for example a monocarboxylic acid, such a hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid or versatic acids (highly branched monocarboxylic acids), or a dicarboxylic acid, for example decanedicarboxylic acid. Benzoic acid and N-cyclohexyldiazenium dioxide (for example in the form of its water-soluble salts) are also suitable. 2-Ethylhexanoic acid is preferred.

The acids can also be used in the form of their salts, for example dimethylalkylamine salts. A water-soluble salt of N-cyclohexyldiazenium dioxide is, for example, the potassium salt.

The wood preservatives are water-miscible, form clear solutions with water and, in the conventional application concentration (from 0.5 to 10.0% by weight, based on the concentrate), have a pH of about 5.0–8.0, in particular 6.0–7.0.

The wood preservatives (concentrates) are more or less viscous solutions whose viscosity can be reduced by adding polar solvents. Examples of suitable polar solvents are dimethylformamide, diethylformamide, N-methyl-pyrrolidone, dimethyl sulfoxide, glycols, polyglycols, glycol ethers, glycol ether acetates and alcohols.

The concentrates generally contain from 5.0 to 75.0, in particular from 30 to 50%, by weight of a $C_6$-$C_{20}$-dimethylalkylamine, from 5.0 to 75.0, in particular from 15 to 25%, by weight of tridemorph or fenpropemorph, from 6.5 to 50.0, in particular from 10 to 75%, by weight of an emulsifier, from 2.5 to 30.0, in particular form 5 to 25%, by weight of a water insoluble acid or its salts and from 0 to 50.0, in particular from 4 to 30%, by weight of a solvent, the sum in each case being 100% by weight. Water may also be present, water being contained, for example, in the commercial form of the emulsifiers.

The following may, for example, also be used: wetting agents, corrosion inhibitors, dyes and, if required, binders.

To improve the range of action of the wood preservatives, organic fungicides, eg. furmecyclox, benodanil, 2-(thiocyanomethylthio)-benzothiazole or 3-iodo-3-propynyl carbamate, or organic insecticides, eg. chlorpyrifos, permethrin or lindane, may also be present.

When basic emulsifiers are used, for example ethoxylated alkylamines, it is possible to incorporate, for example, up to 25% of fungicidal acids or their salts, for example boric acid.

Depending on the danger to the wood, it can be preserved, for example, (a) by spraying the wood with the solution, (b) by dipping the wood in the solution, (c) by impregnating the wood with the aid of pressure difference, for example by the pressure impregnation process or double vacuum impregnation process or (d) by application to the wood with a brush.

In the case of secondary wood products, for example wood cuts, pulps and other industrial products, or cellulose-containing materials which are susceptible to fungal attack, for example intermediates in paper-making and woody annual plants (bargasse or rape), application should be adapted to the technical possibilities.

The activity of the agents in the area of wood preservation extends, for example, to (a) molds (eg. Aspergillus niger)

(b) wood-rot fungi (eg. Chaetomium globosum)

(c) blue mold fungi (eg. Pullularia pullulans)

(d) wood-destroying Basidiomycetes (eg. Serpula lacrymans).

The wood preservatives have a very good fungicidal action, as is evident from the experiments below.

Fresh, sawn pine sapwood which measured 200×50×15 mm and had been deep-frozen up to the beginning of the experiment were used for the experiments.

After thawing out (about 6 hours), the timbers were dipped into the solutions for about 10 sec, placed in a slightly inclined position to allow them to drip off, stored temporarily under cover for about 24 hours under standard conditions of temperature and pressure and then installed in the test area. 10 sample boards were impregnated with the individual test solutions ni the manner described above. Control timbers which had not been impregnated were dipped into pure water.

The test area chosen was a meadow whose grass had been cut short before the test timbers were laid out. The test timbers were placed on two plastic rails, at a height of about 1 cm above the grass.

The test boards exposed to outdoor weathering (rain) were tested after two months (Aug./Sept.).

The fungicidal activity was classified in four categories on the basis of the resulting discoloration and changes in the wood surface:

0 no growth
+ slight surface growth in the form of spots
++ pronounced growth in the form of spots
+++ extensive growth to growth covering entire surface.

COMPARATIVE EXAMPLE A 50.0% of dimethylalkylamine ($C_{12}/C_{14}$-alkyl)
17.5% of lactic acid
20.0% of 1,2-propylene glycol
12.5% of water

| Concentration used Wood preservative (concentrate) = 100% | Nature of test timbers |
|---|---|
| 2.5% | +++ |
| 5.0% | +++ |

COMPARATIVE EXAMPLE B

50% of tridemorph
35% of lactic acid
5% of $H_2O$
10% of 1,2-propylene glycol
4% strength solution, cloudy, pH 3.5

| Concentration used | Nature of test timbers |
|---|---|
| 2% | +++ |
| 4% | +++ |

COMPARATIVE EXAMPLE C

80% of dimethylalkylbenzylammonium chloride (about 40% of $C_{12}$, about 50% of $C_{14}$, about 10% of $C_{16}$)
20% of water

| Concentration used | Nature of test timbers |
|---|---|
| 5.0% | +++ |

COMPARATIVE EXAMPLE D

50% of dimethyldialkylammonium chloride (about 90% of $C_{10}$)
50% of water

| Concentration used | Nature of test timbers |
|---|---|
| 2% | +++ |
| 4% | about 50% +++, about 50% ++ |

Examples according to the invention

EXAMPLE 1

30% of dimethylalkylamine ($C_{12}/C_{14}$)
20% of tridemorph
25% of ethoxylated coconut fatty amine (density 0.96 g/cm$^3$ at 50° C.)
25% of 2-ethylhexanoic acid

| Test timber No. | Nature of test timbers Concentration used | |
|---|---|---|
| | 2% | 4% |
| 1 | ++ | + |
| 2 | + | 0 |
| 3 | + | 0 |
| 4 | + | 0 |
| 5 | 0 | 0 |
| 6 | + | 0 |
| 7 | ++ | 0 |
| 8 | 0 | 0 |
| 9 | 0 | 0 |
| 10 | ++ | 0 |

EXAMPLE 2

30% of dimethylalkylamine ($C_{12}/C_{14}$)
20% of fenpropemorph
25% of ethoxylated coconut fatty amine
25% of 2-ethylhexanoic acid

| Test timber No. | Nature of test timbers Concentration used | |
|---|---|---|
| | 2% | 4% |
| 1 | + | + |
| 2 | + | 0 |
| 3 | 0 | 0 |
| 4 | 0 | 0 |
| 5 | ++ | 0 |
| 6 | + | 0 |
| 7 | 0 | 0 |
| 8 | 0 | 0 |
| 9 | + | 0 |
| 10 | + | 0 |

EXAMPLE 3

29% of dimethylalkylbenzylammonium chloride (about 40% of $C_{12}$, about 50% of $D_{14}$, about 105 of $C_{16}$)
6% of $H_2O$
50% of dimethylalkylamine ($C_{12}/C_{14}$)
20% of 2-ethylhexanoic acid

| Test timber No. | Nature of test timbers Concentration used | |
|---|---|---|
| | 2% | 4% |
| 1 | + | 0 |
| 2 | ++ | + |
| 3 | + | + |
| 4 | + | + |
| 5 | + | 0 |
| 6 | ++ | 0 |
| 7 | 0 | + |
| 8 | 0 | + |
| 9 | + | 0 |
| 10 | + | 0 |

EXAMPLE 4

24% of dimethylalkylbenzylammonium chloride (about 40% of $C_{12}$, about 50% of $C_{14}$, about 10% of $C_{16}$)
6% of $H_2O$
30% of dimethylalkylamine ($C_{12}/C_{14}$)
20% of tridemorph
20% of 2-ethylhexanoic acid

| Test timber No. | Nature of test timbers Concentration used | |
|---|---|---|
| | 2% | 4% |
| 1 | 0 | 0 |
| 2 | + | 0 |
| 3 | + | 0 |
| 4 | + | 0 |
| 5 | + | 0 |
| 6 | 0 | 0 |
| 7 | + | 0 |
| 8 | + | + |
| 9 | + | 0 |
| 10 | 0 | 0 |

EXAMPLE 5

30% of dimethylalkylamine
20% of tridemorph
20% of benzoic acid
5% of 1,2-propylene glycol
25% of ethoxylated coconut fatty amine

| Test timber No. | Nature of test timbers Concentration used | |
|---|---|---|
| | 2% | 4% |
| 1 | + | + |
| 2 | ++ | + |
| 3 | + | + |
| 4 | ++ | 0 |
| 5 | + | 0 |
| 6 | 0 | 0 |
| 7 | 0 | 0 |
| 8 | 0 | + |
| 9 | + | 0 |
| 10 | 0 | 0 |

25% of dimethyldialkylammonium chloride (about 90% of $C_{10}$)
20% of tridemorph
10% of 2-ethylhexanoic acid
35% of water

| Test timber No. | Nature of test timbers Concentration used | |
|---|---|---|
| | 2.5% | 5.0% |
| 1 | + | 0 |
| 2 | 0 | 0 |
| 3 | 0 | 0 |
| 4 | + | 0 |
| 5 | + | 0 |
| 6 | + | + |
| 7 | + | 0 |
| 8 | + | + |
| 9 | + | + |
| 10 | + | 0 |

EXAMPLE 7

25% of dimethyldialkylammonium chloride (about 90% of $C_{10}$)
10% of potassium salt of N-cyclohexyldiazenium dioxide
45% of water

| Test timber No. | Nature of test timbers Concentration used | |
|---|---|---|
| | 2.5% | 5.0% |
| 1 | + | + |
| 2 | + | 0 |
| 3 | + | 0 |
| 4 | 0 | 0 |
| 5 | ++ | + |
| 6 | + | + |
| 7 | + | 0 |
| 8 | 0 | 0 |
| 9 | 0 | 0 |
| 10 | + | 0 |

We claim:
1. An amine-based wood preservative, which comprises an effective amount of a mixture of:
   (a) N,N-dimethyl-N-alkylamine, N-tridecyl-2,6-dimethylmorpholine, 4-(3-(para-tert-butylphenyl)-2-methylpropyl)-2,6-cis-dimethylmorpholine or a mixture thereof,
   (b) an emulsifier, and
   (c) a water-insoluble acid selected from the group consisting of a $C_5$–$C_{20}$ saturated monocarboxylic acid, $C_5$–$C_{20}$ saturated dicarboxylic acid, benzoic acid and N-cyclohexyldiazenium dioxide; or a salt thereof.
2. The wood preservative as claimed in claim 1, wherein said N,N-dimethyl-N-alkylamine has an alkyl group of from 6 to 20 carbon atoms.
3. The wood preservative according to claim 2, wherein said alkyl has from 12 to 14 carbon atoms.
4. The wood preservative as claimed in claim 1, wherein said emulsifier is selected from the group consisting of quaternary ammonium compounds, fatty amine salts, exthoxylated alkyl amines and N-alkyl-1,3-diaminopropanes.
5. The wood preservative according to claim 4, wherein said emulsifier is a quaternary ammonium compound of the formula:

$(R^1R^2R^3R^4N)^+Z^-$ wherein $R^1$ is an alkyl group from 8 to 20 carbon atoms or benzyl, which is unsubstituted or substituted by $C_1$-$C_{20}$-alkyl or halogen; $R^2$ is $C_1$-$C_6$alkyl or $C_3$-$C_9$-alkoxyalkyl; $R^3$ is $C_1$-$C_6$-alkyl or $C_3$-$C_4$-alkoxy and $R^4$ is $C_1$-$C_{20}$-alkyl; or two of the radicals $R^1$, $R^2$, $R^3$ and $R^4$, together with the nitrogen atom, form a heterocyclic radical which contains 4 or 5 carbon atoms, 1 or 2 nitrogen atoms and 1, 2 or 3 double bonds, the carbon atoms being unsubstituted or substituted by $C_1$-$C_4$-alkyl or halogen, with Z being an acid radical.

6. The wood preservative according to claim 1, wherein said water-insoluble acid is selected from the group consisting of hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid, versatic acids, decanedicarboxylic acid, benzoic acid and N-cyclohexyldiazenium dioxide.

7. The wood preservative according to claim 6, wherein said water-insoluble acid is 2-ethylhexanoic acid.

8. The wood preservative according to claim 1, which further comprises a polar solvent selected from the group consisting of dimethylformamide, diethylformamide, N-ethyl-pyrrolidone, dimethylsulfoxide, glycols, polyglycols, glycol ethers, glycol ether acetates and alcohols.

9. The wood preservative according to claim 8, which comprises from 5.0 to 75.0% by weight of a $C_6$-$C_{20}$-dimethylalkylamine, from 5.0 to 75.0% by weight of tridemorph or fenpropemorph, from 6.5 to 50.0% by weight of an emulsifier, from 2.5 to 30.0% by weight of said water-insoluble acid or a salt thereof, and up to 50.0% by weight of a polar solvent, the sum being 100% by weight.

10. The wood preservative according to claim 9, which comprises from 30 to 50% by weight of a $C_6$-$C_{20}$-dimethylalkylamine, from 15 to 25% by weight of tridemorph or fenpropemorph, from 10 to 75% by weight of an emulsifier, from 5 to 25% by weight of said water-insoluble acid or a salt thereof and from 4 to 30% by weight of said polar solvent, the sum being 100% by weight.

11. The wood preservative according to claim 1, which further comprises a fungicide or an insecticide.

12. The wood preservative according to claim 1, which is in the form of an aqueous solution having a concentration of from 0.5% to 10.% by weight, and having a pH of about 5.0 to 8.0.

13. A method for protecting wood from fungi, which comprises treating said wood with an effective amount of the wood preservative of claim 5.

14. The method according to claim 13, wherein said treating of said wood comprises spraying wood with said wood preservative, dipping said wood into said wood preservative, impregnating said wood with said wood preservative and applying said wood preservative to said wood with a brush.

15. The method according to claim 13, wherein said treated wood comprises freshly sawn timber, freshly felled wood, wood cuts, pulps or cellulose-containing materials which are susceptible to fungal attack.

* * * * *